(12) United States Patent
Shakespeare et al.

(10) Patent No.: US 7,573,575 B2
(45) Date of Patent: Aug. 11, 2009

(54) SYSTEM AND METHOD FOR COLOR MEASUREMENTS OR OTHER SPECTRAL MEASUREMENTS OF A MATERIAL

(75) Inventors: Tarja T. Shakespeare, Kuopio (FI); John F. Shakespeare, Kuopio (FI)

(73) Assignee: Honeywell International Inc., Morristown, NJ (US)

( * ) Notice: Subject to any disclaimer, the term of this patent is extended or adjusted under 35 U.S.C. 154(b) by 286 days.

(21) Appl. No.: 11/601,039

(22) Filed: Nov. 17, 2006

(65) Prior Publication Data
US 2007/0153278 A1  Jul. 5, 2007

Related U.S. Application Data

(63) Continuation-in-part of application No. 11/362,582, filed on Feb. 24, 2006.

(60) Provisional application No. 60/754,694, filed on Dec. 29, 2005.

(51) Int. Cl.
*G01B 11/00* (2006.01)
(52) U.S. Cl. .................................... 356/402
(58) Field of Classification Search ................ 356/402
See application file for complete search history.

(56) References Cited

U.S. PATENT DOCUMENTS

| 4,006,358 | A | 2/1977 | Howarth |
| 4,288,691 | A | 9/1981 | Horton |
| 4,376,946 | A | 3/1983 | Kaminow et al. |
| 4,439,038 | A | 3/1984 | Mactaggart |
| 4,565,444 | A | 1/1986 | Mactaggart |
| 4,592,043 | A | 5/1986 | Williams |
| 4,634,928 | A | 1/1987 | Figueroa et al. |
| 4,699,510 | A | 10/1987 | Alguard |

(Continued)

FOREIGN PATENT DOCUMENTS

DE        3148076 A1    6/1983

(Continued)

OTHER PUBLICATIONS

Tarja Shakespeare et al., "Problems in Colour Measurement of Fluorescent Paper Grades", Analytica Chimica Acta 380 (1999), pp. 227-242.

(Continued)

*Primary Examiner*—Roy Punnoose
(74) *Attorney, Agent, or Firm*—Munck Carter, LLP

(57) ABSTRACT

A system and method for color measurements or other spectral measurements of a material are provided. An illuminating device generates light for illuminating a sample of material. A detector detects light that has interacted with the sample and provides a measurement of the light that has interacted with the sample. A controller adjusts a duty cycle of the illuminating device to control the illumination of the sample. The measurement could be used by an analyzer to determine a spectral characteristic of the sample (such as a color of the sample). The determination of the spectral characteristic could be done without using any measurement of light that has not interacted with the sample. One or multiple light emitting diodes (LEDs) could be used to illuminate the sample, and the duty cycle of individual LEDs or groups of LEDs could be adjusted.

21 Claims, 10 Drawing Sheets

U.S. PATENT DOCUMENTS

| | | | |
|---|---|---|---|
| 4,715,715 A | 12/1987 | Howarth et al. | |
| 4,786,817 A | 11/1988 | Boissevain et al. | |
| 4,807,630 A | 2/1989 | Malinouskas | |
| 4,856,014 A | 8/1989 | Figueroa et al. | |
| 4,883,963 A | 11/1989 | Kemeny et al. | |
| 4,928,013 A | 5/1990 | Howarth et al. | |
| 4,944,594 A | 7/1990 | Burk | |
| 5,000,569 A * | 3/1991 | Nylund | 356/237.1 |
| 5,015,099 A | 5/1991 | Nagai et al. | |
| 5,047,652 A | 9/1991 | Lisnyansky et al. | |
| 5,122,974 A | 6/1992 | Chance | |
| 5,137,364 A | 8/1992 | McCarthy | |
| 5,235,192 A | 8/1993 | Chase et al. | |
| 5,313,187 A | 5/1994 | Choi et al. | |
| 5,338,361 A | 8/1994 | Anderson et al. | |
| 5,400,258 A | 3/1995 | He | |
| 5,642,189 A | 6/1997 | Alguard | |
| 5,642,192 A | 6/1997 | Gordon et al. | |
| 5,774,213 A | 6/1998 | Trebino et al. | |
| 5,793,486 A | 8/1998 | Gordon et al. | |
| 5,795,394 A | 8/1998 | Belotserkovsky et al. | |
| 5,821,536 A | 10/1998 | Pettit | |
| 5,933,243 A | 8/1999 | Hagen | |
| 5,963,333 A | 10/1999 | Walowit et al. | |
| 5,992,318 A | 11/1999 | DiBello et al. | |
| 6,058,201 A | 5/2000 | Sikes et al. | |
| 6,074,483 A | 6/2000 | Belotserkovsky et al. | |
| 6,142,629 A * | 11/2000 | Adel et al. | 351/206 |
| 6,222,172 B1 * | 4/2001 | Fossum et al. | 250/205 |
| 6,263,291 B1 | 7/2001 | Shakespeare et al. | |
| 6,272,440 B1 | 8/2001 | Shakespeare et al. | |
| 6,448,550 B1 * | 9/2002 | Nishimura | 250/226 |
| 6,466,839 B1 | 10/2002 | Heaven et al. | |
| 6,499,402 B1 | 12/2002 | Sikes et al. | |
| 6,556,305 B1 | 4/2003 | Aziz et al. | |
| 6,584,435 B2 | 6/2003 | Mestha et al. | |
| 6,603,551 B2 | 8/2003 | Mestha et al. | |
| 6,639,669 B2 * | 10/2003 | Hubble et al. | 356/319 |
| 6,670,103 B2 | 12/2003 | Chang | |
| 6,724,473 B2 | 4/2004 | Leong et al. | |
| 6,743,337 B1 | 6/2004 | Ischdonat | |
| 6,763,322 B2 | 7/2004 | Potyrailo et al. | |
| 6,805,899 B2 | 10/2004 | MacHattie et al. | |
| 6,856,436 B2 | 2/2005 | Brukilacchio et al. | |
| 6,894,442 B1 | 5/2005 | Lim et al. | |
| 6,914,684 B1 * | 7/2005 | Bolash et al. | 356/600 |
| 6,949,734 B2 | 9/2005 | Neff et al. | |
| 7,218,656 B2 * | 5/2007 | Nishimura | 372/38.02 |
| 7,291,856 B2 | 11/2007 | Haran et al. | |
| 2001/0052978 A1 * | 12/2001 | Lewis et al. | 356/326 |
| 2003/0058441 A1 | 3/2003 | Shakespeare et al. | |
| 2004/0119781 A1 | 6/2004 | Szumla | |
| 2004/0212804 A1 | 10/2004 | Neff et al. | |
| 2004/0260520 A1 | 12/2004 | Braendle et al. | |
| 2005/0065400 A1 | 3/2005 | Banik et al. | |
| 2005/0276291 A1 * | 12/2005 | Nishimura | 372/38.02 |
| 2006/0006821 A1 * | 1/2006 | Singer et al. | 315/312 |
| 2006/0237156 A1 | 10/2006 | Shakespeare et al. | |
| 2006/0243931 A1 | 11/2006 | Haran et al. | |
| 2006/0255300 A1 | 11/2006 | Shakespeare | |
| 2007/0108846 A1 * | 5/2007 | Ashdown | 307/149 |
| 2007/0139735 A1 | 6/2007 | Shakespeare et al. | |
| 2007/0144388 A1 | 6/2007 | Shakespeare et al. | |
| 2007/0153277 A1 | 7/2007 | Shakespeare et al. | |

FOREIGN PATENT DOCUMENTS

| | | |
|---|---|---|
| DE | 19515499 A1 | 10/1996 |
| DE | 19643474 A1 | 5/1997 |
| EP | 0 319 158 A1 | 6/1989 |
| EP | 1437222 A1 | 7/2004 |
| EP | 1457335 A1 | 9/2004 |
| EP | 1 491 877 A1 | 12/2004 |
| WO | WO 02/47438 A2 | 6/2002 |
| WO | WO 03/037111 A1 | 5/2003 |

OTHER PUBLICATIONS

Tarja Shakespeare et al., "Advanced Colour Control Through Reflectance Optimization", Proceedings 2nd EcoPaperTech Conference, Helsinki Finland, Jun. 1998, pp. 183-194.

Stokman et al., "Color Measurement by Imaging Spectrometry", Computer Vision & Image Understanding, San Diego, CA, US, vol. 79, No. 2, Aug. 2000, pp. 236-249.

Wandell, "Color Measurement and Discrimination", Journal of the Optical Society of America, USA, vol. 2, No. 1, Jan. 1985, pp. 62-71.

* cited by examiner

SYSTEM AND METHOD FOR COLOR MEASUREMENTS OR OTHER SPECTRAL MEASUREMENTS OF A MATERIAL

CROSS-REFERENCE TO RELATED APPLICATIONS

This application is a continuation-in-part of U.S. patent application Ser. No. 11/362,582 entitled "COLOR SENSOR" filed on Feb. 24, 2006, which claims priority to U.S. Provisional Patent Application Ser. No. 60/754,694 filed on Dec. 29, 2005. Both of these applications are hereby incorporated by reference.

TECHNICAL FIELD

This disclosure relates generally to color measurement systems and more specifically to a system and method for color measurements or other spectral measurements of a material.

BACKGROUND

Sheets of material are often used in various industries and in a variety of ways. These materials can include paper, plastic, and other materials manufactured or processed in webs or sheets, such as long sheets of paper collected in reels. The processing of these materials can include printing text, images, and other content on a sheet of paper or other material. These sheets of material are often manufactured or processed at a high rate of speed, such as up to thirty meters per second or more.

It is often necessary or desirable to measure one or more characteristics of a sheet of material as the sheet is being manufactured or processed. For example, in a paper sheet-making process, it is often desirable to measure the color of the paper sheet to verify whether the sheet has a color that is within specification. As another example, in a printing process, it is often desirable to measure the color of the printing on a sheet to verify whether the printed color is within specification.

SUMMARY

This disclosure provides a system and method for color measurements or other spectral measurements of a material.

In a first embodiment, a system includes an illuminating device operable to generate light for illuminating a sample of material. The system also includes a detector operable to detect light that has interacted with the sample and to provide a measurement of the light that has interacted with the sample. In addition, the system includes a controller operable to adjust a duty cycle of the illuminating device to control the illumination of the sample.

In particular embodiments, the illuminating device includes multiple light emitting diodes (LEDs), and the controller is operable to adjust the duty cycle of individual LEDs or groups of LEDs.

In other particular embodiments, the system includes an analyzer operable to determine a spectral characteristic of the sample based on the measurement of the light that has interacted with the sample. The analyzer does not use, when determining the spectral characteristic of the sample, any measurement of light that has not interacted with the sample.

In a second embodiment, a method includes illuminating a sample of material using at least one light emitting diode (LED). The method also includes detecting light that has interacted with the sample and providing a measurement of the light that has interacted with the sample. In addition, the method includes adjusting a duty cycle of the at least one LED to control the illumination of the sample.

In a third embodiment, a system includes at least one light emitting diode (LED) operable to generate light for illuminating a sample of material. The system also includes a detector operable to detect light that has interacted with the sample and to provide a measurement of the light that has interacted with the sample. The system further includes an analyzer operable to determine a spectral characteristic of the sample using the measurement of the light that has interacted with the sample. In addition, the system includes a controller operable to adjust the at least one LED to control the illumination of the sample. The analyzer, to determine the spectral characteristic of the sample, does not use any measurement of light that has not interacted with the sample.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
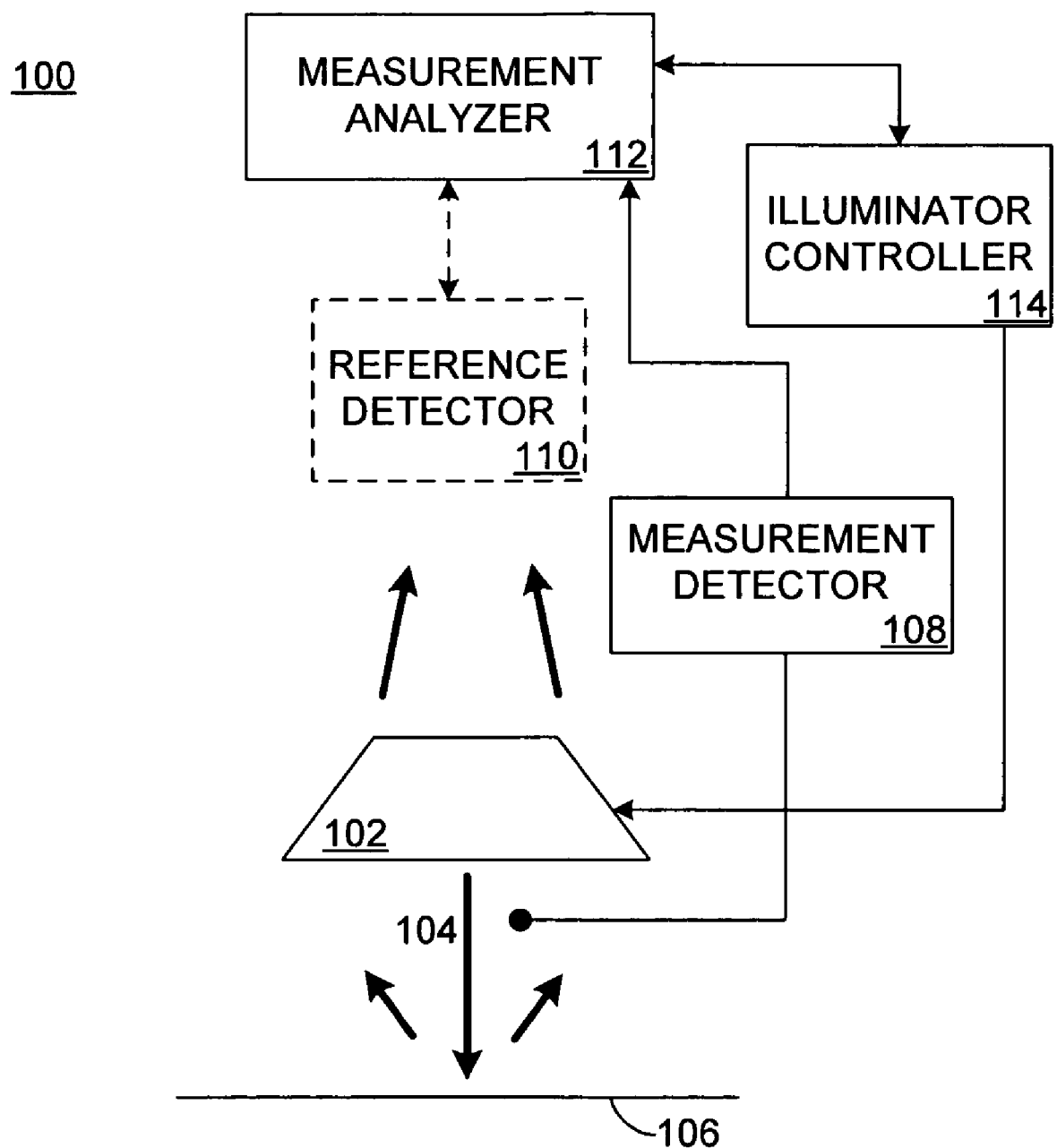
FIG. 1 illustrates a first example color measurement system for measuring color according to one embodiment of this disclosure.

FIG. 1 illustrates a first example color measurement system 100 for measuring color according to one embodiment of this disclosure. The embodiment of the color measurement system 100 shown in FIG. 1 is for illustration only. Other embodiments of the color measurement system 100 could be used without departing from the scope of this disclosure.

As shown in FIG. 1, the color measurement system 100 includes one or more illuminating devices 102. Each illuminating device 102 generates and provides a light beam 104, which illuminates at least part of a sample 106. The light beam 104 could have any suitable wavelength or range of wavelengths, such as light within a visible range or an ultraviolet range. As a particular example, the light beam 104 could represent a collimated beam of light. The illuminating device 102 includes any suitable structure for generating light.

In some embodiments, an illuminating device 102 includes one or more light emitting diodes (LEDs). The LEDs may emit light at one or more wavelengths or wavelength ranges, and the LEDs may emit light in a continuous or intermittent manner. In particular embodiments, multiple LEDs can be used in an illuminating device 102, and the LEDs may or may not emit light having different spectrums. When multiple LEDs are used, individual LEDs can be illuminated (possibly independent of other LEDs) to control the wavelength spectrum of light emitted by the illuminating device 102. The LEDs could represent any suitable light emitting diode or diodes, such as large surface area LEDs formed from arrays of miniature LEDs in a honeycomb structure. The LEDs could also support individually controlled wavelength bands, such as red-green-blue LEDs. The LEDs could further represent broadband emitters, such as those constructed using multiple phosphors or incorporating quantum dots.

In these embodiments, an illuminating device 102 could include additional components in addition to the LEDs. For example, the illuminating device 102 could include heat sink panels, optical elements, one or more circuit boards on which the LEDs are mounted, and mechanical arrangements for mounting the device 102. The optical elements may include beam-shaping optics, such as micro-lenses, micro-reflectors, micro-diffusers, and spectral filters. The illuminating device 102 could be configured to allow for the replacement of part or all of the illuminating device 102 at regular intervals or when needed (such as when diagnostic tests indicate degraded performance). Different illuminating devices 102 may have different LED types and combinations.

The light beam 104 generated by the illuminating device 102 is directed at the sample 106. The sample 106 may represent any suitable portion of a material or materials being analyzed, such as a material where the color or other spectral properties are being determined. The sample 106 could represent a variety of materials handled in a manufacturing, mechanized, or other process. Example samples 106 could include a web of paper or board, a sheet or film of plastic, or a woven or non-woven fabric. A web of material could be continuously moved throughout a process (such as a paper production or printing process) using rollers, presses, and other machinery. The sample 106 could be transparent, translucent, or opaque. While the sample 106 may be described in this document as a sheet or web of paper, the sample 106 is not limited to sheets or webs of paper. Also, a sample 106 representing a sheet of material could represent an individual sheet of material that is advanced on a conveyor belt or other device(s) for transporting sheets of material, or the sample 106 could represent multiple sheets of material. The sample 106 could further represent a portion of a continuous sheet of material or a discrete sample placed manually for measurement.

In this example embodiment, the light beam 104 is reflected off of the sample 106 and measured by a measurement detector 108. A portion of the light beam 104 produced by the illuminating device 102 may also be directed to a reference detector 110, which measures the portion of the light beam 104 from the illuminating device 102. Each of the detectors 108-110 measures light in any suitable manner, such as by measuring the spectral power distribution of the received light. Each of the detectors 108-110 includes any suitable structure for measuring light, such as structures for converting collected light into electrical charges. In some embodiments, the detectors 108-110 may use optic fiber, micro optics, or other mechanisms to collect light to be detected by the detectors 108-110. Moreover, spectral filters or other elements such as dichroic beam splitters may be used to modify the spectral power distribution of the collected light before it is detected. These can be used, for instance, to exclude spectral bands that are undesirable for a measurement detector 108 or to divide the light between plural detectors responsive to different spectral ranges. Also, the measurement detector 108 could measure the spectral power distribution of light in multiple wavelength bands substantially spanning at least the visible light range.

The detectors 108-110 may be formed from or represent a variety of devices, such as charge-coupled devices (CCD), charge injection devices (CID), digital Complementary Metal Oxide Semiconductor (CMOS) photodiode arrays, discrete photodiodes, or any other suitable light sensitive device(s). Output signals generated by the detectors 108-110 may be analog or digital, such as an analog signal converted to a digital signal for processing.

In particular embodiments, the measurement detector 108 and the reference detector 110 could represent spectrometers. A spectrometer may include a spectrograph (containing a light entrance port and a dispersive element such as a grating) and a detector. The dispersive element could include a linear variable filter or a set of discrete optical filters of known characteristics. The spectrometer may have additional optical elements (such as mirrors or beam splitters) to direct a beam of light towards the dispersive element, distribute the beam across the dispersive element, or focus dispersed light onto a detector. The detector in a spectrometer could represent a linear CCD detector with photodiodes (such as 128 to 2,048 photodiodes), a two-dimensional array of photodiodes, or a set of discrete photodetectors. A spectrometer may isolate an approximately collimated portion of a light beam and disperse the light beam into multiple wavelength bands using the dispersive element. The spectrometer may also distribute the dispersed light onto the detector so that specific wavelength bands are directed at or incident on specific positions of the detector. The detector may detect and quantify the light falling on multiple positions of the detector and produce spectral measurements from which calorimetric data may be derived. In other particular embodiments, the detectors 108-110 could represent spectrocolorimeters, which could produce as output only colorimetric data (such as tristimulus values and derived calorimetric data like brightness data).

In this example, the measurement detector 108 may measure the spectrum of light reflected from the sample 106. The measured light represents light from the illuminating device 102 that has illuminated the sample 106 and interacted with the sample 106 by being reflected from the sample 106. Depending on the sample 106, the reflected light could include fluorescent emission or phosphorescent emission from the sample 106 in response to the illumination.

The reference detector 110 may measure the spectrum of light from the illuminating device 102. This light has not interacted with the sample 106 or with a calibration standard. The input to the reference detector 110 may represent a portion of the light beam 104 produced by the illuminating device 102.

The measurement detector 108 and the reference detector 110 supply the measured values of light (such as measured spectral power distributions or weighted averages of spectral ranges) to a measurement analyzer 112. The measurement analyzer 112 uses the values of light from the detectors 108-110 to determine the color of the sample 106. However, as noted below, the reference detector 110 could be omitted from a color measurement system, and the measurement analyzer 112 could use values of light from only the measurement detector 108 to determine the color of the sample 106. For example, the measurement analyzer 112 could use measurement data from the detectors 108-110 to determine a radiance transfer factor matrix for the sample 106, which can be used to determine the color of the sample 106 under a specified lighting condition. The measurement analyzer 112 could use the determined color in any suitable manner, such as comparing the determined color to a specified color or color range (such as a desired color or range) or outputting the determined color for use by an external system. The measurement analyzer 112 could include any hardware, software, firmware, or combination thereof for determining a color of a sample 106.

An illuminator controller 114 controls the operation of the illuminating device 102, thereby controlling the illumination of the sample 106. Depending on the implementation, the measurement analyzer 112 may regulate the illuminator controller 114, such as when the measurement analyzer 112 directs the illuminator controller 114 to cause the illuminating device 102 to emit light in different relative intensities at each of multiple wavelength bands. The illuminator controller 114 could also operate independent of the measurement analyzer 112. The illuminator controller 114 includes any hardware, software, firmware, or combination for controlling one or more illuminating devices, such as LEDs.

The illuminator controller 114 may control the operation of the illuminating device 102 in any suitable manner. For example, LEDs in the illuminating device 102 may be controlled by altering the current and/or voltage used to drive the LEDs, which may influence the relative spectral power distribution and/or the total power of light emitted by the LEDs. Also, altering the duty cycle (the percentage of time an LED is activated during a specified period) of the LEDs can be used to alter the average spectral power distribution of light emitted by the LEDs. Using one or both of these techniques, the illuminator controller 114 could control the spectral power distribution of the light provided by the illuminating device 102. When controlling the duty cycle of the LEDs, the LEDs can be switched on and off at any suitable rate, which can include the use of rapid switching such as microsecond switching. Moreover, the instants at which this switching takes place need not necessarily be separated by equal time intervals. While periodic switching at a fixed frequency may be advantageous in some embodiments, the switching can be performed in any arbitrary periodic or aperiodic sequence that achieves the desired duty cycle. Also, if multiple LEDs are used, the duty cycle of one or some of the LEDs can be varied in a different manner than the duty cycle of one or some others of the LEDs. In particular embodiments, the illuminator controller 114 regulates the timing of at least one LED so that the LED is switched on for less than an entire measurement interval. The timing of switching the LED can be controlled so as to achieve a desired average spectral power distribution for illumination during that measurement interval. The measurement interval is that time during which the detector accumulates received light to form a measurement. This interval need not necessarily be of a fixed duration, and the interval can be formed by combining detection from plural subintervals that need not necessarily be contiguous in time.

As noted above, the color measurement system 100 may or may not include the reference detector 110. The reference detector 110 could be omitted from the color measurement system 100, for example, when LEDs are used in the illuminating device 102. This is because the spectral power distribution of light provided by LEDs may be known ahead of time, so the reference detector 110 may not be needed to determine the spectral power distribution of light provided by the LEDs.

In one aspect of operation, the color measurement system 100 may determine the color of the sample 106 by directing the beam of light 104 at the sample 106 to illuminate at least part of the sample 106. The color measurement system 100 may then detect and measure the light that has interacted with the sample 106. The interaction of the light beam 104 with the sample 106 may include absorption, scattering, and excitation of fluorescent emission. The detection and measurement of light that has interacted with the sample 106 may occur on the same side of the sample 106 as the illumination, on the opposite side of the sample 106 than the illumination, or on both sides of the sample 106 (either simultaneously or sequentially). In this example, the measurement detector 108 measures the light reflected from the sample 106 on the same side of the sample 106 as the illumination.

The portion of the sample 106 from which light is directed to the measurement detector 108 may be called the "viewed area." The viewed area could represent a circular disk with a radius of 10 mm, but it may be larger or smaller and need not be circular or contiguous. The illuminated portion of the sample 106 could include the entire viewed area and may include an additional area bounding the viewed area. The illuminated portion of the sample 106 could even include the entire sample 106. The illumination could be spatially uniform over at least the viewed area, both in intensity and in spectral power distribution at any measurement instant.

The reference detector 110 may provide a reference point for the measurement analyzer 112. The reference detector 110 may be positioned to receive an accurate sample of the light emitted by the illuminating device 102. In some embodiments, the reference detector 110 may use an optical fiber to gather light directly from the illuminating device 102 or from the edges of the beam 104. The optical fiber may prevent reflected light from corrupting the light sample measured by the reference detector 110. The reference detector 110 may have the same or similar light detecting structure as the measurement detector 108.

Depending on the configuration, the light measured by the reference detector 110 may have essentially the same spectral power distribution as the light provided to the sample 106. For example, the light beam 104 produced by the illuminating device 102 can be divided between these two purposes, but it need not be divided in equal amounts. As particular examples, optical fibers, optical mirrors, or achroic beam splitters may cause a portion of the light from the illuminating device 102 to be directed to the reference detector 110 and another portion to be directed to illuminate the sample 106. As another particular example, a multi-ported integrating sphere (the internal surface of which is diffusely reflective) may be used to combine light from the illuminating device 102, supply a specific fraction of the combined light to the reference detector 110, and supply another portion of the combined light to illuminate the sample 106. Instead of a sphere, a partial sphere or other suitable shape may also be used, and the number and positions of light entry ports and light exit ports can be chosen appropriately.

The illuminating device(s) 102 and the detectors 108-110 could have any suitable arrangement or geometry in the color measurement system 100. The measurement geometry is the geometric arrangement relative to the sample 106 of the light incident on the sample 106 and the light from the sample 106 incident on the measurement detector 108. There are numerous measurement geometries in common use. Some have been formalized in international standards, including 0/45, 45/0, 0/d, and d/0 arrangements. The first number in each arrangement represents the angle (in degrees relative to the sample 106) at which the sample 106 is to be illuminated. The second number is the angle (in degrees relative to the sample 106) at which light from the sample 106 is to be measured. By convention, the 0° angle in these arrangements is taken to be perpendicular to the sample 106 being illuminated. The designation "d" indicates that the illumination or measurement is to be diffuse or non-directional. For directional illumination at angles greater than 0°, the illumination may be from a single azimuth direction, from multiple azimuth directions, or from a circular annulus.

The measurement analyzer 112 may compare the intensity and spectrum of light measured by the detectors 108-110 with known values of intensity and spectrum of light for at least one calibration tile of known properties. By illuminating at least one calibration tile and measuring the light at both the reference detector 110 and the measurement detector 108, it is possible to form a relation between the photometric scales of the detectors 108-110. For example, a normalizing ratio for the detectors 108-110 can be determined for each spectral band. After that, in measuring a sample 106, the relation between these photometric scales can be used to obtain a total radiance factor measurement from the measurements made at the detectors 108-110. The total radiance factor measurement can be used to determine the color of the sample 106. In some embodiments, the measurement analyzer 112 may use a stored table, equations, or a combination thereof to compute the characteristics of the sample 106.

In particular embodiments, LEDs form the illuminating device 102, and the LEDs may be regulated so as to produce one or more illumination states for the measurements. The measurement analyzer 112 may determine the characteristics of the sample 106 by determining the ratio of the reflecting light beam intensity and/or spectrum to the intensity and/or spectrum of the illuminating light beam 104 from the illuminating device 102. After compensating for the relation between photometric scales, the ratio of the light measured at the measurement detector 108 to the light measured at the reference detector 110 may represent the total radiance factor of the sample 106 for the illuminator used for that particular measurement.

The color to be determined for the sample 106 may depend on one or more specified illumination states for the sample 106. For example, a specification for a paper product may define an acceptable color or color range, but the specification may define an illumination state to be used when determining if the actual color of the paper product is acceptable. Depending on the implementation, the color of the sample 106 may be determined for an illuminator that matches an illumination state used in a measurement. The color of the sample 106 may also be determined for an illuminator that does not match any illumination state used in the measurements, such as one expressed as a linear combination of different illumination states used in the measurements. The color of the sample 106 may further be determined for a specified illuminator that does not match any illumination state used in the measurements and that is not expressible exactly as a linear combination of illumination states used in the measurements. In this last case, the color may be determined as belonging to an interval or range of colors that are defined by a set of linear combinations of illumination states used in the measurements, where the set forms a set of perturbations approximating the specified illuminator. The color may be determined for the sample 106 itself, for an infinitely thick opaque pad formed of similar samples 106, for the sample 106 itself with a backing having known optical properties, or in any other suitable manner.

In particular embodiments, the measurement analyzer 112 could include a processor, a memory, and one or more input/output interface devices. A local interface (such as a network interface) may have additional elements, such as controllers, buffers (caches), drivers, repeaters, and receivers that enable communications. Further, the local interface may include address, control, and/or data connections to enable appropriate communications among the components of a network. The measurement analyzer 112 could also include software used with a computer or other suitable operating device (such as the processor). The measurement analyzer 112 could further include or support a graphical user interface (GUI) to enable interactions with a user. For example, the GUI could allow an administrator or other user to enter, view, and store the characteristics of the sample 106 or to enter constraints for controlling components of the color measurement system 100 or a manufacturing process. In addition, the measurement analyzer 112 could be separate from the other components of the color measurement system 100 (which could collectively form a single measurement device). The measurement analyzer 112 is not limited just to reflectance measurements of color and can measure transmittance measurements of color or both characteristics simultaneously.

Depending on the implementation, the illuminator controller 114 may be incorporated in or governed by the measurement analyzer 112, or it may be an autonomous unit. The illuminator controller 114 may control the light output from the illuminating device 102 (such as an LED or group of LEDs) by controlling the voltage and/or current supplied to the LED or group of LEDs. The illuminator controller 114 may also control the light output from the illuminating device 102 by controlling the duty cycle of the LED or group of LEDs, such as by controlling the amount of time that the LED or group of LEDs produces light during a measurement. In some embodiments, the illuminating device 102 may be operated in a continuously-on mode or in an intermittent mode, such as in a flashing on-off mode. In the continuously-on mode, the power for the illuminating device 102 may be fixed or varied (such as varied as a function of time according to a deterministic schedule or in a random or pseudo-random sequence). In the continuously-on mode, the illuminating device 102 may be intermittently switched off, such as between measurement intervals. In the flashing on-off mode, the power for the illuminating device 102 may be fixed or varied from flash to flash (such as varied according to a deterministic schedule or in a random or pseudo-random sequence). The operating mode, voltage, current, power, timing, duty cycle, and so forth may or may not be the same for all LEDs.

In particular embodiments, an autonomous illuminator controller 114 operates the LEDs in a fixed sequence of states, where each state has a specified duration. Also, for each state, a voltage, current, duty cycle, or power may be defined for each LED or group of LEDs, and a timing may be defined for switching each LED or group of LEDs on and off. For example, in a first state lasting 10 ms, a first LED may be continuously on with a current of 200 mA, a second LED may be flashing on-off at 1000 Hz with a flash current of 2 A and a flash duration of 100 µs, and a third LED may be continuously on with current rising linearly from 100 mA to 300 mA. In a second state lasting 5 ms, the first and second LEDs could both be continuously on where each has a current of 150 mA, and the third LED can be switched off.

The illuminator controller 114 may also perform thermal management of the LEDs, such as by monitoring their temperatures and by operating heating or cooling devices to keep the LED temperatures within acceptable limits. For example, the LEDs could be heated by switching them on at times when measurements are not being made.

The color measurement system 100 can be calibrated from time to time, such as during a calibration that occurs periodically or whenever possible. This may be done, for example as described above, to determine the relation between the photometric scales of the detectors 108-110. The calibration could include the use of one or more calibration tiles, such as an opaque white tile with known high reflectivity at all wavelengths of interest. During calibration, a calibration tile could be placed in the same position in which the sample 106 to be measured is normally located. However, this is not a necessity if the optical path is folded or otherwise compensated by other means. In that case, a calibration tile could be located elsewhere, even "inside" a measurement instrument, in a position that is optically equivalent to the position of the sample 106.

The color measurement system 100 and its various other embodiments may comply with any of the various standards used in the appropriate industry. These standards could include Technical Association of the Pulp and Paper Industry (TAPPI) standards, as well as any other industry, government, or other standards.

Figure 2:
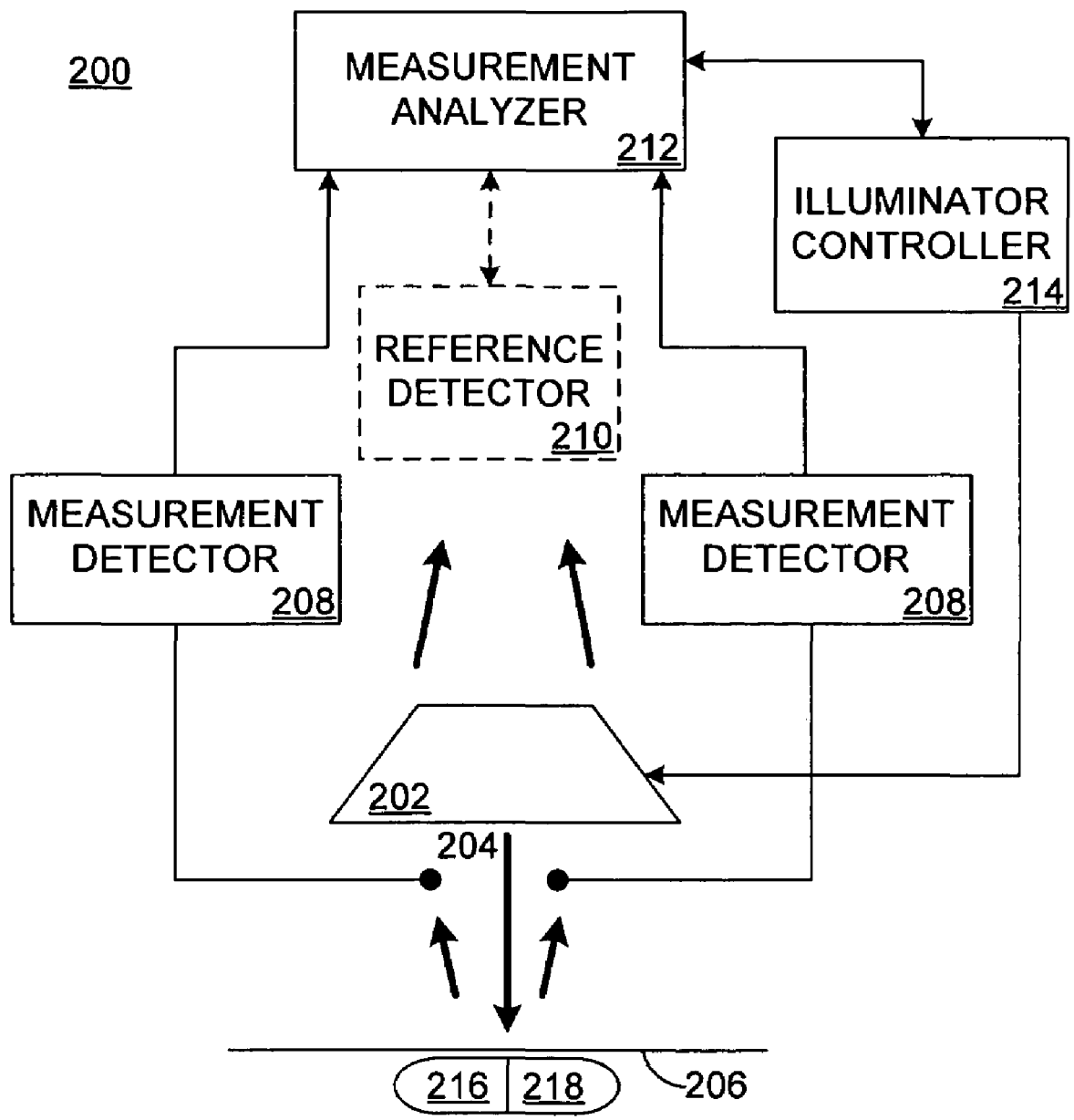
FIG. 2 illustrates a second example color measurement system for measuring color according to one embodiment of this disclosure.

FIG. 2 illustrates a second example color measurement system 200 for measuring color according to one embodiment of this disclosure. The embodiment of the color measurement system 200 shown in FIG. 2 is for illustration only. Other embodiments of the color measurement system 200 could be used without departing from the scope of this disclosure.

The color measurement system 200 is similar to the color measurement system 100 of FIG. 1. As shown in FIG. 2, the color measurement system 200 includes an illuminating device 202 for providing a light beam 204 to illuminate a sample 206. The illuminating device 202 may provide a focused beam of light or collimated light beam, such as by utilizing one or more LEDs. Reflected beams of light are detected and measured by multiple measurement detectors 208. The measurement detectors 208 supply measured values of light to a measurement analyzer 212. A reference detector 210 may be used to provide a reference point for the measurement analyzer 212.

The measurement analyzer 212 uses the values of light to determine the characteristics of the sample 206. The measurement analyzer 212 may also regulate an illuminator controller 214, which controls the illuminating device 202. The illuminator controller 214 could also operate independent of the measurement analyzer 212. The illuminator controller 214 could cause the illuminating device 202 to emit different wavelengths or intensities of light. The components of the color measurement system 200 may incorporate aspects as previously described with respect to the color measurement system 100 of FIG. 1.

As noted above, the reference detector 210 may be used to provide a reference point for the measurement analyzer 212. The reference detector 210 may be positioned to receive an accurate sample of the light emitted by the illuminating device 202. In particular embodiments, the reference detector 210 may use a trapezoid mirror and/or other micro lens and optical components to gather light directly from the illuminating device 202 or from the edges of the light beam 204. The trapezoid mirror may prevent reflected light from corrupting the reference. In other embodiments, the reference detector 210 can be omitted from the color measurement system 200.

In this example embodiment, the sample 206 has a first backing 216 and a second backing 218. The backings 216-218 may allow the measurement analyzer 212 to determine characteristics of the sample 206 based on the reflected light associated with the different backings 216-218. For example, the backings 216-218 could represent a backing of known low reflectivity and a backing of known high reflectivity, respectively. As a particular example, the first backing 216 may be black, and the second backing 218 may be white. In these embodiments, the scattering, absorption, and/or fluorescent emission spectra of the sample 206 can be inferred from simultaneous measurements of remitted light made above the backing of known low reflectivity and the backing of known high reflectivity. For a translucent sample 206, reflectance measurements with black and white backings can be utilized with the Kubelka-Munk method to estimate true reflectance for an infinitely thick pad formed of the sample 206. The Kubelka-Munk method can also be extended to accommodate fluorescence in the color estimation. This could also be done using a measurement of remitted light above a backing of known reflectivity and a simultaneous measurement of transmitted light on the non-illuminated side of the sample 206 (which can be done as described below).

Figure 3:
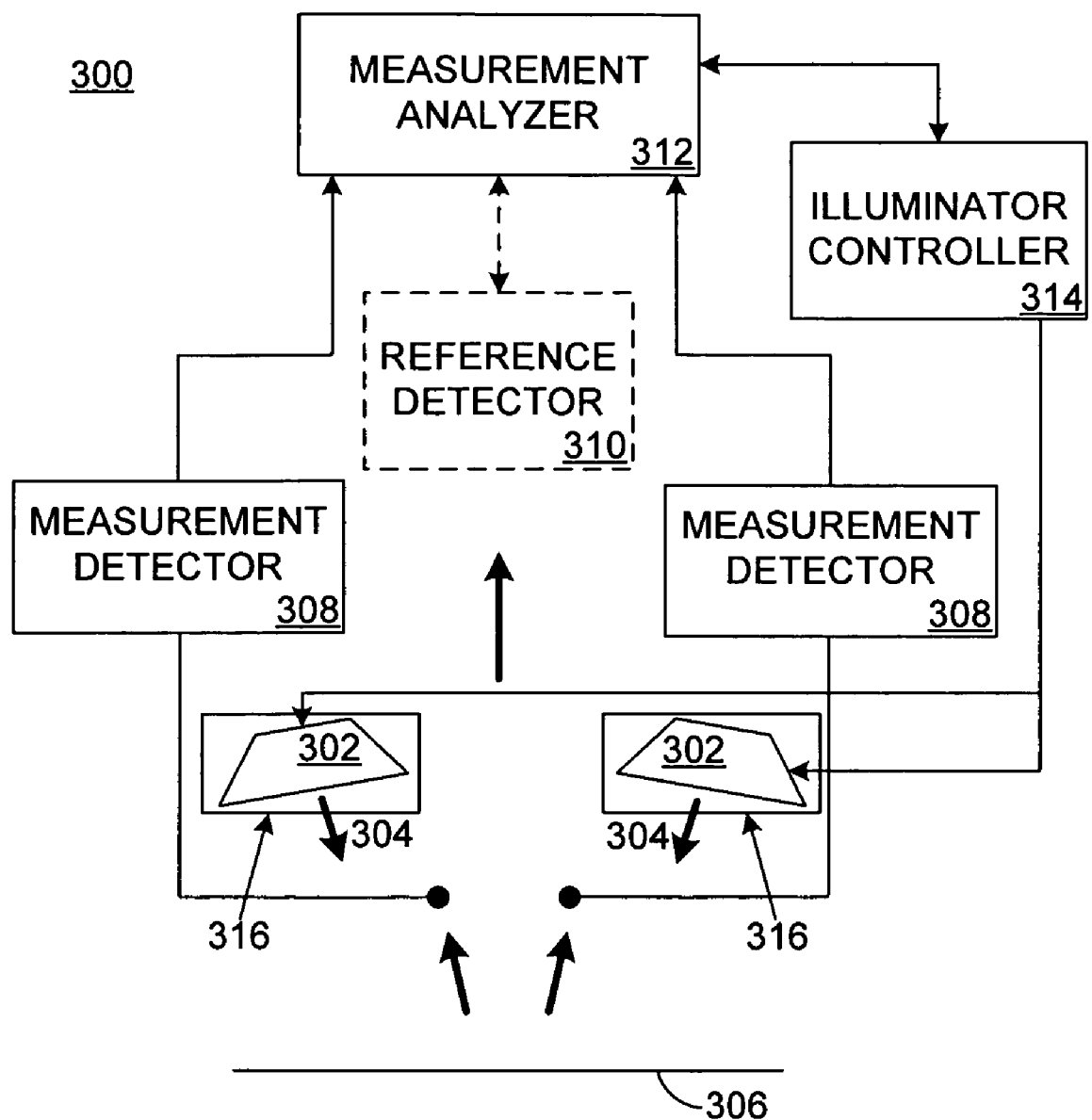
FIG. 3 illustrates a third example color measurement system for measuring color according to one embodiment of this disclosure.

FIG. 3 illustrates a third example color measurement system 300 for measuring color according to one embodiment of this disclosure. The embodiment of the color measurement system 300 shown in FIG. 3 is for illustration only. Other embodiments of the color measurement system 300 could be used without departing from the scope of this disclosure.

The color measurement system 300 is similar to the color measurement systems 100 and 200 of FIGS. 1 and 2. As shown in FIG. 3, the color measurement system 300 includes multiple illuminating devices 302 for providing multiple light beams 304 to illuminate a sample 306. Each illuminating device 302 could provide a focused beam of light or collimated light beam, such as by utilizing one or more LEDs. In this example embodiment, the LEDs may be located on multiple circuit boards 316. In particular embodiments, the circuit boards 316 may include LEDs that emit different spectrums or wavelengths of light. For example, one circuit board 316 may include LEDs that emit light in the visible spectrum, while another circuit board 316 may include LEDs that emit light in the ultraviolet spectrum. The circuit boards 316 may also include LEDs that emit light from different directions. The circuit boards 316 may make it possible to replace LEDs without requiring all LEDs of the color measurement system 300 to be replaced at the same time. For example, an administrator may replace the ultraviolet LEDs on a more regular interval.

Reflected beams of light are detected and measured by multiple measurement detectors 308. Each measurement detector 308 supplies measured values of light to a measurement analyzer 312. A reference detector 310 may be used to provide a reference point for the measurement analyzer 312. The measurement analyzer 312 uses the values of detected light to determine the characteristics of the sample 306. The measurement analyzer 312 may also regulate an illuminator controller 314, or the illuminator controller 314 could operate independently. For example, the measurement analyzer 312 may direct the illuminator controller 314 to cause the illuminating devices 302 to emit light in different relative intensities at each of multiple wavelength bands. The components of the color measurement system 300 may incorporate aspects as previously described with respect to the color measurement systems 100 and 200.

The reference detector 310 may be positioned to receive an accurate sample of the light emitted by illuminating device

302. In some embodiments, the reference detector 310 may detect light at a location between the circuit boards 316 to gather light directly from the illuminating device 302. In other embodiments, the reference detector 310 may be omitted from the color measurement system 300.

Figure 4A:
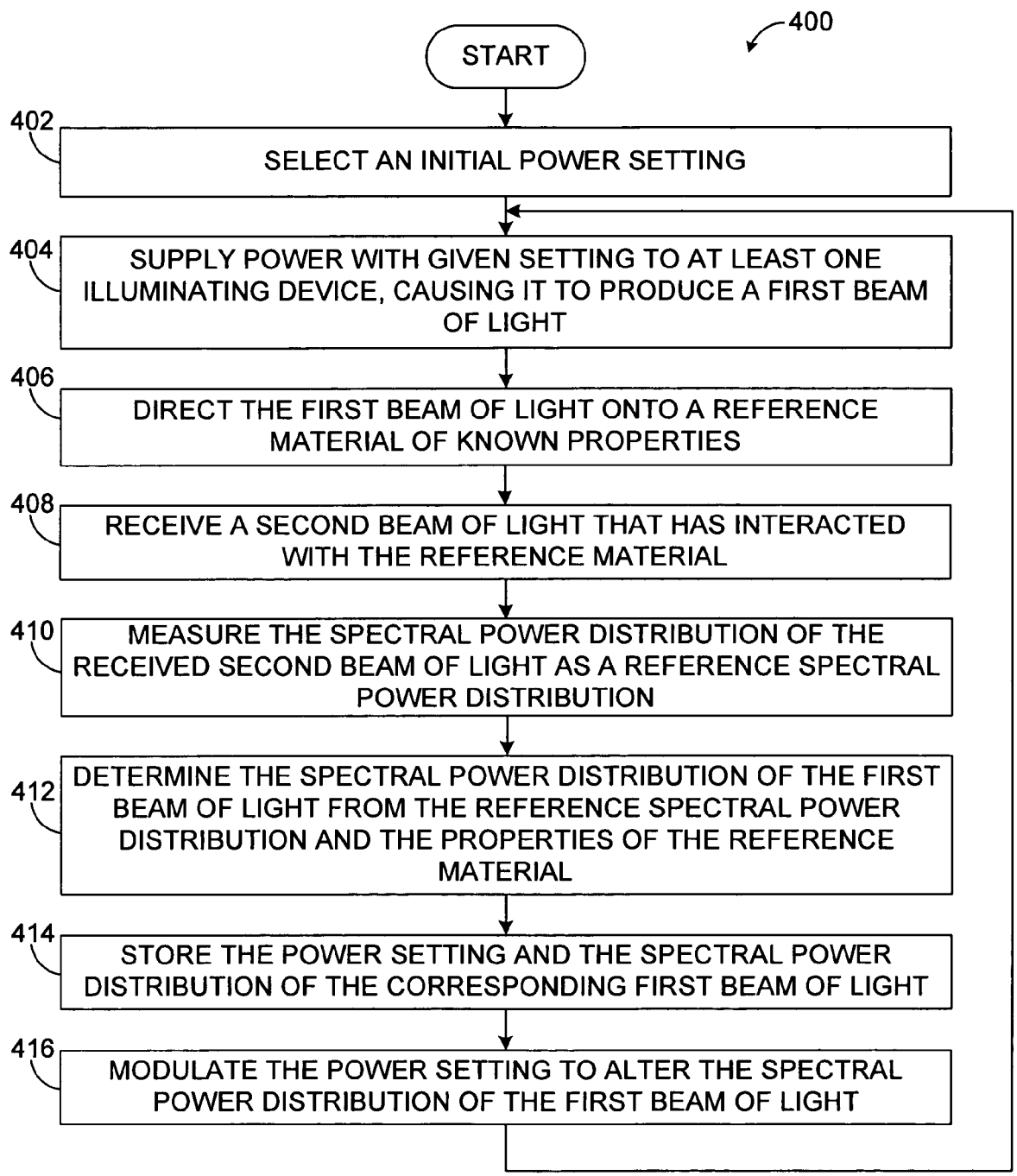
FIGS. 4A and 4B illustrate a first example method for measuring color according to one embodiment of this disclosure.
Figure 4B:
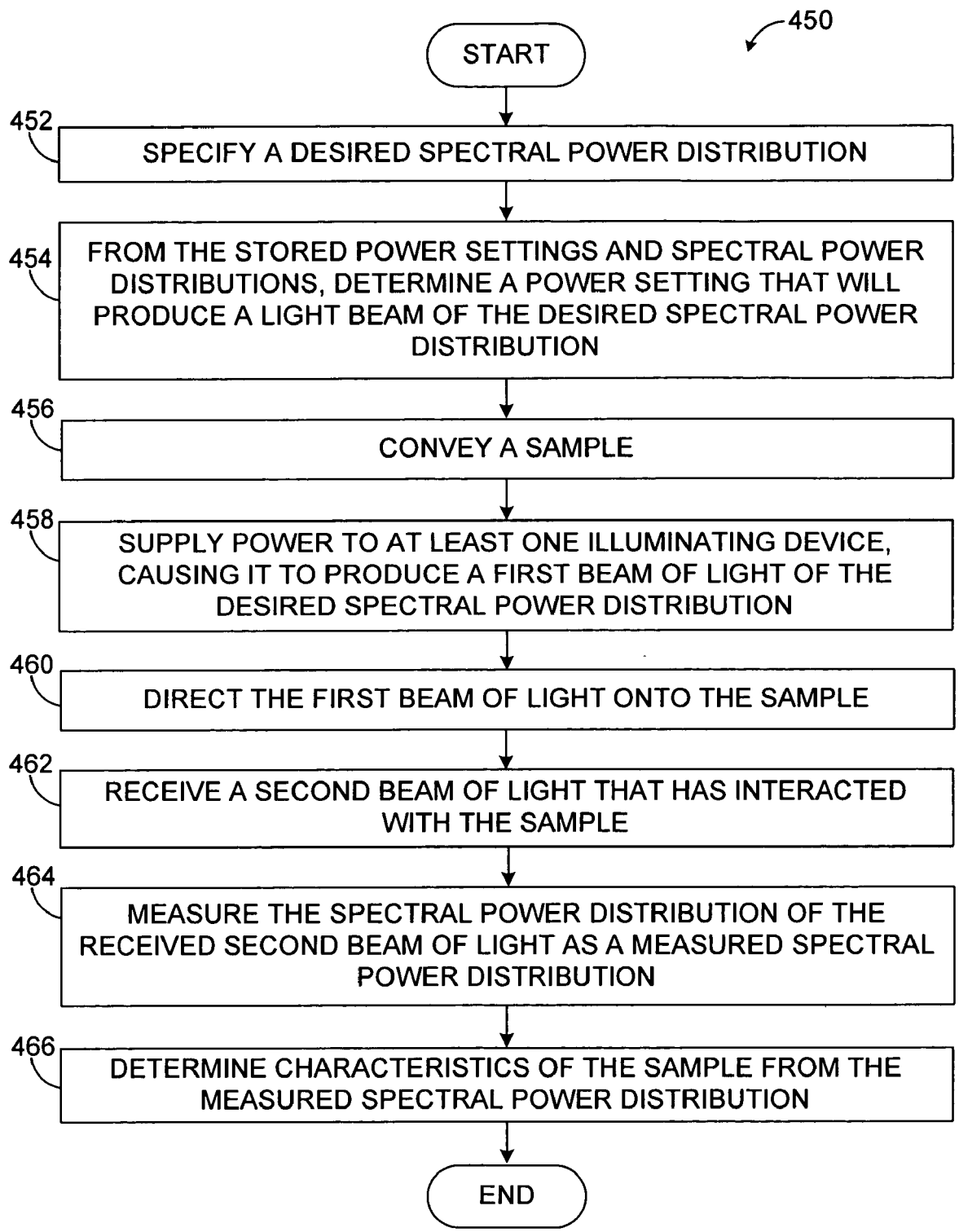

FIGS. 4A and 4B illustrate a first example method for measuring color according to one embodiment of this disclosure. More specifically, FIG. 4A illustrates an example method 400 for calibrating a color measurement system, and FIG. 4B illustrates an example method for determining the color of a sample using the color measurement system. The embodiments of the methods 400, 450 shown in FIGS. 4A and 4B are for illustration only. Other embodiments of the methods could be used without departing from the scope of this disclosure.

As shown in FIGS. 4A and 4B, there may be two phases to measuring the color of a sample, a calibration phase (shown in FIG. 4A) in which parameters of the color measurement system are determined and an operation phase (shown in FIG. 4B) in which the color measurement system is used to measure the sample.

As shown in FIG. 4A, in the calibration phase, an initial power setting is selected at step 402. Power with this setting is supplied to an illuminating device (such as 102, 202, 302), causing the illuminating device to produce a first beam of light (such as 104, 204, 304) at step 404. The first beam of light is directed onto a reference material of known properties at step 406. The reference material may, for example, represent a diffusely reflecting material of known high reflectance through at least the visible range. The reference material may also represent a fluorescent material of known fluorescence characteristics and known reflectance in the excitation and emission bands of its fluorescence.

A second beam of light that has interacted with the reference material is received at step 408, and the spectral power distribution of the received second beam is measured at step 410. This could include using one or more measurement detectors (such as 108, 208, 308) to measure the spectral power distribution of light reflected from the reference material. The spectral power distribution of the first beam of light is determined from the measured spectral power distribution of the second beam of light and the known properties of the reference material at step 412. The power setting and the determined spectral power distribution of the first beam of light are stored at step 414.

The power setting is modulated so as to alter the spectral power distribution of the first beam of light at step 416. This could include adjusting the voltage or current used to drive LEDs or the duty cycle of the LEDs. The method 400 then returns to step 404 to supply power with the new settings to the illuminating device, and steps 404-414 are repeated for the new setting. Steps 404-416 could be repeated a number of times so that a variety of power settings and corresponding spectral power distributions are determined and stored. The steps may be repeated using the same or multiple reference materials, such as reference materials having different fluorescence characteristics.

Once the calibration phase has been performed at least once, the color measurement system can be used in an operation phase to determine the color of a sample. As shown in FIG. 4B, a desired spectral power distribution for illumination is specified at step 452. From the stored power settings and stored spectral power distributions obtained in the calibration phase, a power setting is determined that should cause the illuminating device to produce light of the desired spectral power distribution at step 454. A manufacturing or other process advances a sample (such as 106, 206, 306) to the appropriate location, such as to a pass-line of the color measurement system, at step 456.

An illuminator controller (such as 114, 214, 314) supplies power with the determined settings to an illuminating device, causing it to produce a first beam of light of the desired spectral power distribution at step 458. This may be accomplished by supplying power to selected LEDs of the illuminating device. The power could have a specified voltage and/or current level, or the power could have a specified duty cycle.

The illuminating device directs the first beam of light onto the sample at step 460. The first beam of light interacts with the sample to produce a second beam of light, which is received by at least one measurement detector at step 462. The at least one measurement detector measures the spectral power distribution of the received second beam of light at step 464. A measurement analyzer (such as 112, 212, 312) determines the characteristics of the sample from the spectral power distribution of the second beam of light at step 466. If necessary, the measurement analyzer may change the desired spectral power distribution for illumination during operation and may employ measurements made by illuminating the sample with a single spectral power distribution or with each of two or more spectral power distributions in determining characteristics of the sample.

The calibration phase may be repeated from time to time, for example, so that the effects of component aging can be compensated for and performance degradation can be avoided. In particular embodiments, one or more suitable reference materials may be contained within the measurement apparatus with a mechanism that deploys it/them into the measurement position or that alters the light path of the first and second light beams so that the calibration can be performed with minimal disturbance to normal operation.

Although FIGS. 4A and 4B illustrate one example of a method for measuring color, various changes may be made to FIGS. 4A and 4B. For example, while shown as a series of steps, various steps in FIGS. 4A and 4B could overlap or occur in parallel. As a particular example, steps 452 and 456 could occur in parallel with step 454. Also, although not shown, the color measurement system could use a reference detector (such as 110, 210, 310) during calibration or during normal operation. In addition, both methods could involve the use of one or multiple illuminating devices or measurement detectors.

Figure 5A:
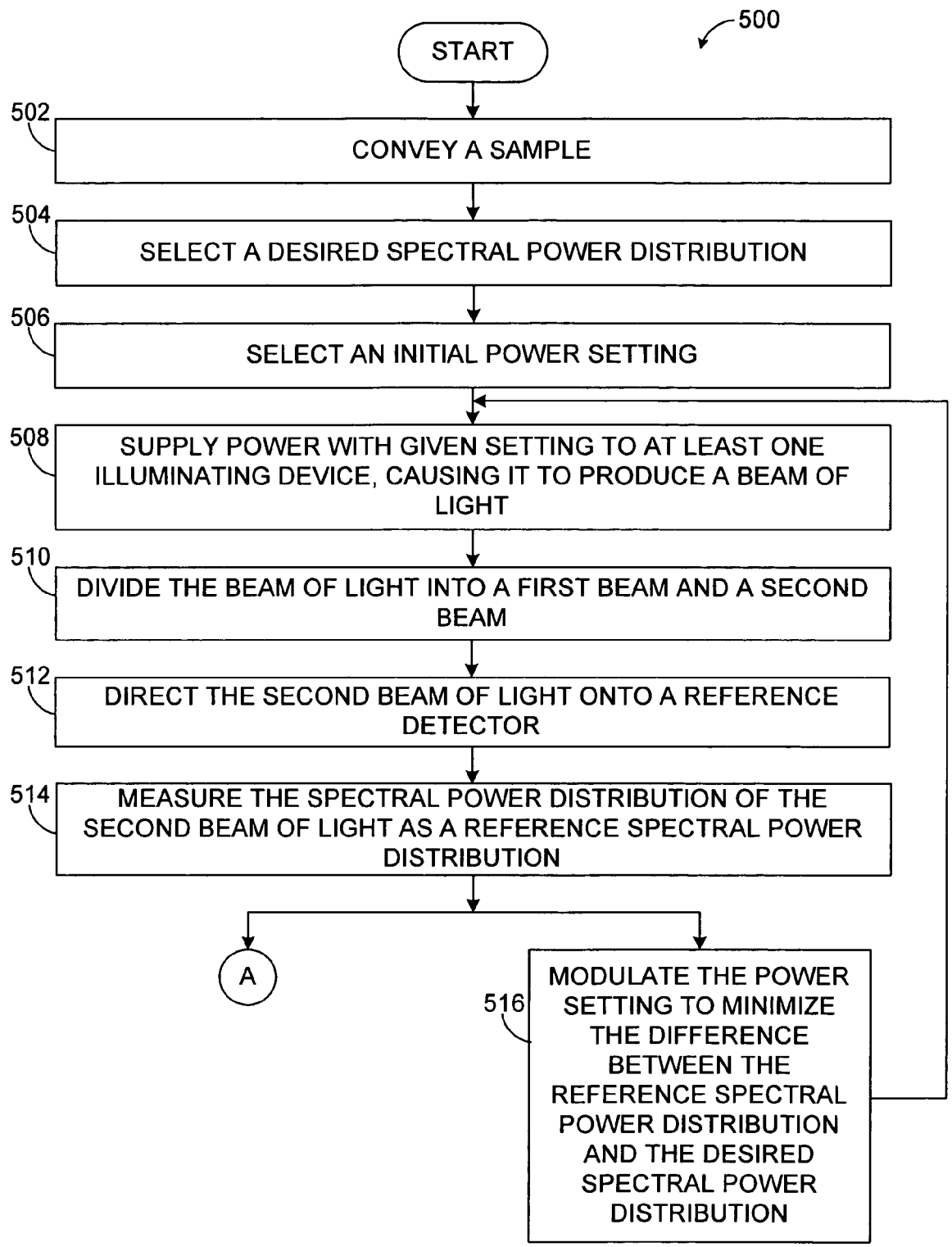
FIGS. 5A and 5B illustrate a second example method for measuring color according to one embodiment of this disclosure.
Figure 5B:
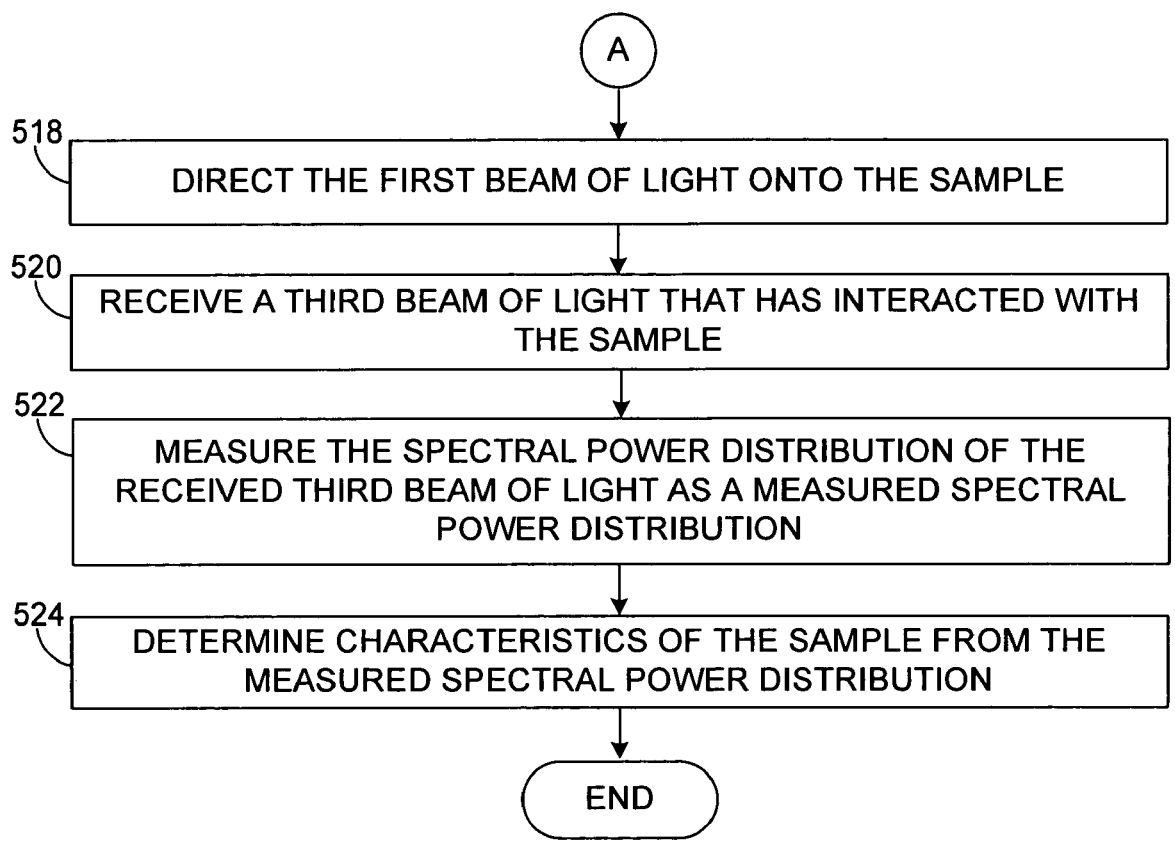

FIGS. 5A and 5B illustrate a second example method 500 for measuring color according to one embodiment of this disclosure. The embodiment of the method 500 shown in FIGS. 5A and 5B is for illustration only. Other embodiments of the method could be used without departing from the scope of this disclosure.

A manufacturing or other process advances a sample to the appropriate location in a color measurement system at step 502. A desired spectral power distribution for illumination is selected at step 504. An initial power setting for the desired spectral power distribution is selected at step 506. An illuminator controller supplies power with the given power setting to an illuminating device, causing it to produce a beam of light at step 508.

The beam of light is divided into a first beam and a second beam at step 510. The first beam and the second beam need not have the same total power, but their relative spectral power distributions could be the same at least in the visible range. The second beam of light is directed onto a reference detector (such as 110, 210, 310) at step 512. The reference detector measures the spectral power distribution of the second beam as a reference spectral power distribution at step 514.

The illuminator controller modulates the power setting of the illuminating device so as to minimize the difference between the measured reference spectral power distribution and the desired spectral power distribution at step 516. Steps 508-516 could then be repeated until the difference between the measured reference spectral power distribution and the desired spectral power distribution is sufficiently small (such as within a specified threshold). These steps could also be repeated whenever the illuminator controller selects a different desired spectral power distribution for illumination. The steps may further be repeated from time to time during operation to ensure that the spectral power distribution used for illumination does not deviate from the desired spectral power distribution.

The first beam of light is directed onto the sample at step 518. A third beam of light, which has interacted with the sample, is received by a measurement detector at step 520. The measurement detector measures the spectral power distribution of the received third light beam, producing a measured spectral power distribution at step 522. When the reference spectral power distribution is sufficiently close to the desired spectral power distribution, the characteristics of the sample can be determined from the measured spectral power distribution by a measurement analyzer at step 524. The measurement analyzer may change the desired spectral power distribution for illumination during operation and may employ measurements made by illuminating the sample with a single desired spectral power distribution or with each of multiple desired spectral power distributions in determining characteristics of the sample. The power setting that minimizes the difference between the reference spectral power distribution and the desired spectral power distribution can be stored by the measurement analyzer or by the illuminator controller for later use. A stored power setting for a desired spectral power distribution can be used as an initial power setting if the measurement analyzer selects the same desired spectral power distribution at a later time.

Although FIGS. 5A and 5B illustrate another example of a method for measuring color, various changes may be made to FIGS. 5A and 5B. For example, while shown as including both series and parallel steps, various steps in FIGS. 5A and 5B could be rearranged into serial or parallel steps. As a particular example, steps 518-524 could occur in series with step 516, such as after step 516 has modulated the power supply to an acceptable setting. Also, while shown as using a reference detector, the color measurement system could omit the use of a reference detector. In addition, the method 500 could involve the use of one or multiple illuminating devices or measurement detectors.

Figure 6:
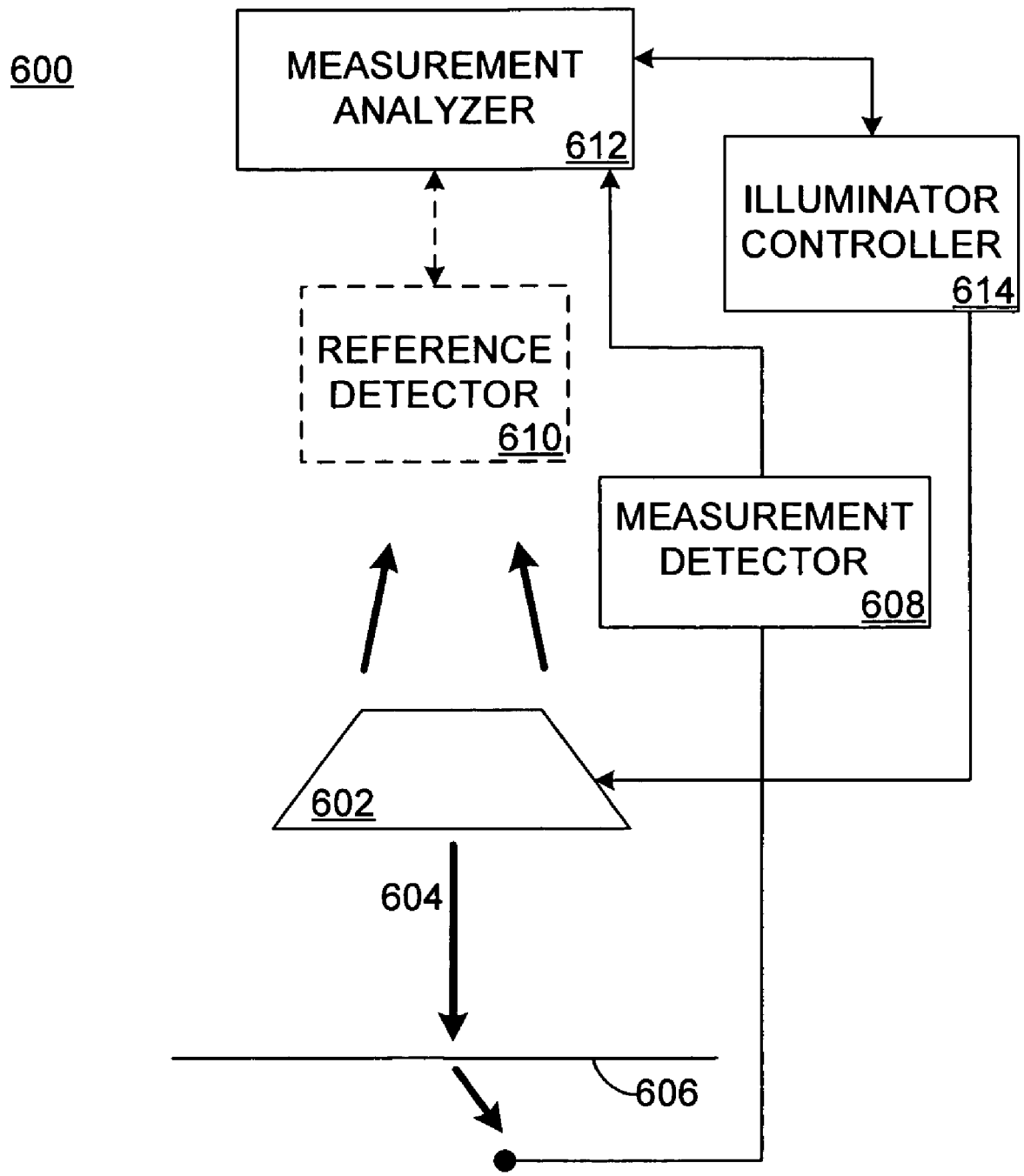
FIG. 6 illustrates a fourth example color measurement system for measuring color according to one embodiment of this disclosure.

FIG. 6 illustrates a fourth example color measurement system 600 for measuring color according to one embodiment of this disclosure. The embodiment of the color measurement system 600 shown in FIG. 6 is for illustration only. Other embodiments of the color measurement system 600 could be used without departing from the scope of this disclosure.

The color measurement system 600 is similar to the color measurement systems 100-300 of FIGS. 1-3. As shown in FIG. 6, the color measurement system 600 includes an illuminating device 602 for providing a light beam 604 to illuminate a sample 606. The illuminating device 602 may provide a focused beam of light or collimated light beam, such as by utilizing one or more LEDs.

The light transmitted through the sample 606 is detected by a measurement detector 608. In this example, the measurement detector 608 may be located or measure the light behind the sample 606 with respect to the illumination of the sample 606. The measurement detector 608 supplies measured values of light to a measurement analyzer 612. A reference detector 610 may be used to provide a reference point for the measurement analyzer 612. The measurement analyzer 612 uses the values of detected light to determine the characteristics of the sample 606. The measurement analyzer 612 may also regulate an illuminator controller 614, or the illuminator controller 614 could operate independently. The measurement analyzer 612 may direct the illuminator controller 614 to cause the illuminating device 602 to emit light in different relative intensities at each of multiple wavelength bands. The components of the color measurement system 600 may incorporate aspects as described above for the other color measurement systems. In this example, the reference detector 610 may be positioned to receive an accurate sample of the light emitted by the illuminating device 602. In other embodiments, the reference detector 610 could be omitted from the color measurement system 600.

Figure 7:
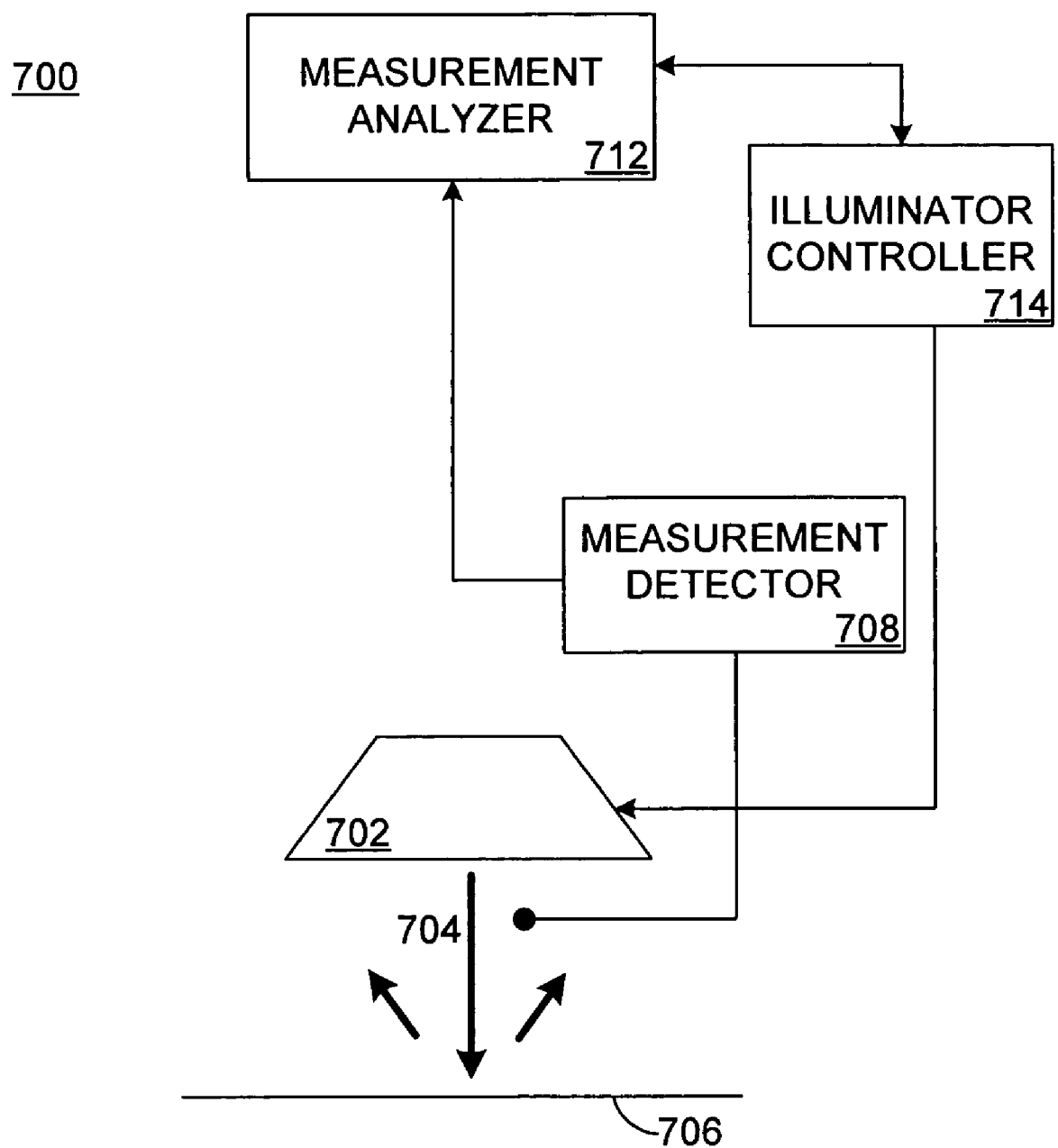
FIG. 7 illustrates a fifth example color measurement system for measuring color according to one embodiment of this disclosure.

FIG. 7 illustrates a fifth example color measurement system 700 for measuring color according to one embodiment of this disclosure. The embodiment of the color measurement system 700 shown in FIG. 7 is for illustration only. Other embodiments of the color measurement system 700 could be used without departing from the scope of this disclosure.

The color measurement system 700 is similar to the color measurement systems described above. As shown in FIG. 7, the color measurement system 700 includes an illuminating device 702 for providing a light beam 704 to illuminate a sample 706. The illuminating device 702 may provide a focused beam of light or collimated light beam, such as by utilizing one or more LEDs. A reflected beam of light is detected by a measurement detector 708. The measurement detector 708 supplies measured values of light to a measurement analyzer 712. The measurement analyzer 712 may determine the color of the sample 706 and may or may not control an illumination controller 714.

As shown here, no reference detector is used in the color measurement system 700. In this embodiment, the radiance transfer factor matrix used to determine the color of the sample 706 can be computed from multiple measurements with a range of illumination states. This can be done without a reference detector if the illumination states used for computing the radiance transfer factor employ LEDs only since the spectral power distribution of illumination is known deterministically from the operating parameters of the LEDs. In particular embodiments, the set of illumination states used can be chosen so as to allow the most reliable, statistically most accurate (highest confidence), or statistically most robust (lowest sensitivity to perturbation) estimate of the expected radiance transfer factor from a given number of measurements.

In particular embodiments, the measurement analysis methods disclosed in U.S. patent application Ser. No. 09/957,085 (which is hereby incorporated by reference) can be used for computation of various properties from measurements with multiple illumination states. For example, an illuminator-independent radiance transfer factor may be computed from measurements with a sufficient number of illumination states. The total radiance factor, fluorescent emission spectrum, and calorimetric quantities for any specified illumination states may be computed from this radiance transfer factor. Moreover, indices of color inconstancy or indices of metamerism between two or more specified illumination states may also be computed from this radiance transfer factor. These methods can be used with or without a reference detector since, if all illumination in an illumination state is achieved using LEDs, the illumination spectrum for that state can be known without using a reference detector.

Although FIGS. 1-3, 6, and 7 illustrate various examples of different color measurement systems for measuring color, various changes may be made to these figures. For example, a combination of the systems from these figures could be used. As a particular example, a system could include multiple measurement detectors in front and behind a sample, with or without one or more backings. Also, various components in the color measurement systems can be combined, further subdivided, or omitted and additional components could be added according to particular needs. As an example, the measurement analyzer could be integrated with the illuminator controller into a single functional unit.

Figure 8:
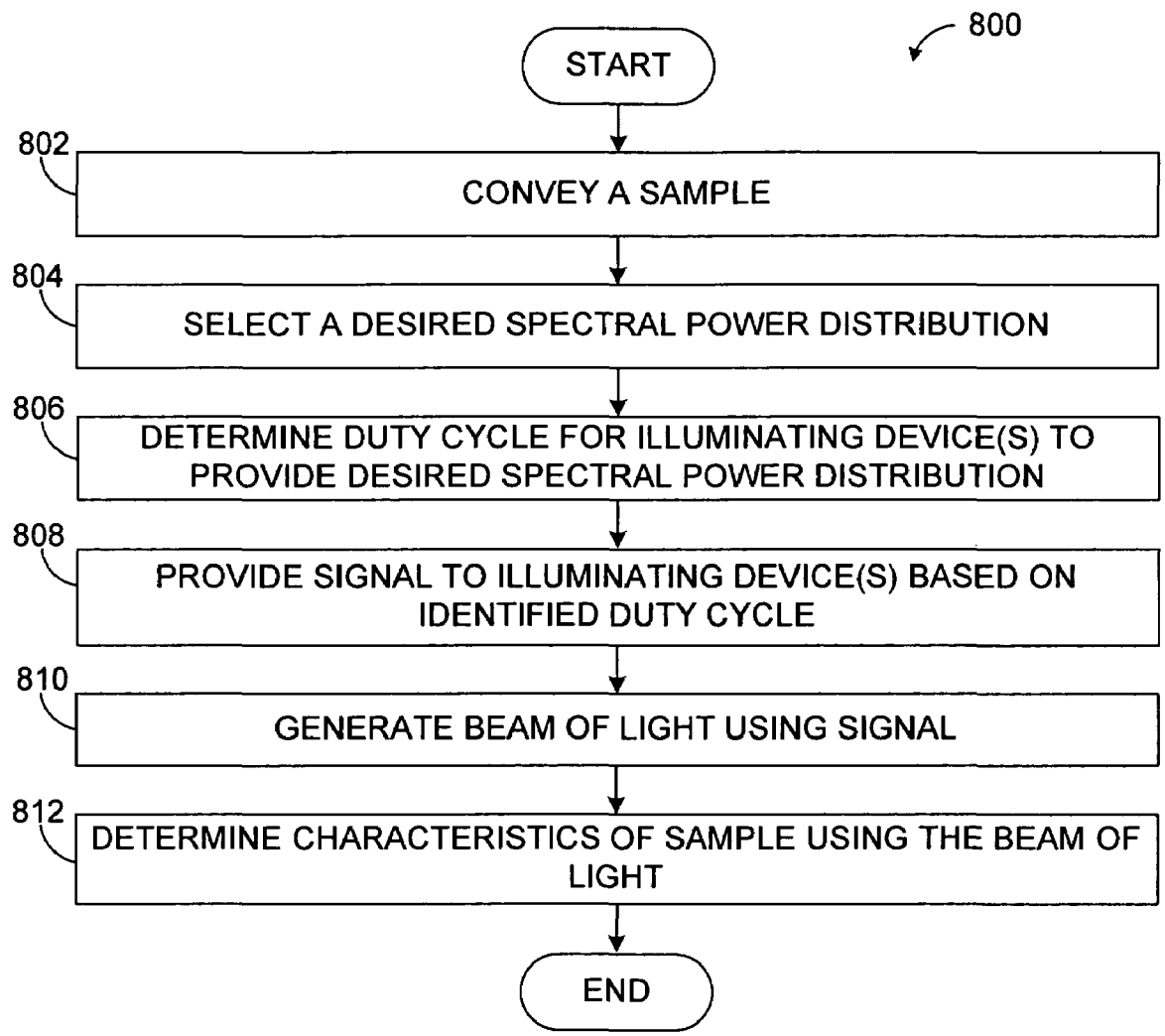
FIG. 8 illustrates a third example method for measuring color according to one embodiment of this disclosure.

FIG. 8 illustrates a third example method 800 for measuring color according to one embodiment of this disclosure. The embodiment of the method 800 shown in FIG. 8 is for illustration only. Other embodiments of the method 800 could be used without departing from the scope of this disclosure.

A manufacturing or other process advances a sample to the appropriate position of a color measurement system at step 802. A desired spectral power distribution for illumination is selected at step 804.

A duty cycle for one or more illuminating devices is determined for providing the desired spectral power distribution at step 806. This could include an illuminator controller determining the duty cycle of a power supply signal, control signal, or other signal provided to one or more LEDs. For example, a desired average spectral power distribution can be achieved during a measurement interval by operating an LED so that it is switched on for less than the whole measurement interval. The desired average spectral power distribution can also be achieved during a measurement interval by operating multiple LEDs so that they are not all switched on for the same amount of time during the measurement interval.

A signal is provided to one or more illuminating devices based on the identified duty cycle at step 808. This could include the illuminator controller providing a power supply signal, control signal, or other signal to one or more LEDs in the illuminating device. The illuminating device generates a beam of light using the signal from the illuminator controller at step 810. One or more characteristics of the sample being tested are determined using the beam of light at step 812. This could include a measurement analyzer using measurements from one or more measurement detectors that measure light reflected or transmitted by the sample. Measurements from a reference detector may or may not be needed.

In this way, one or more LEDs can be operated with a duty cycle of less than 100% relative to a measurement interval. Also, multiple LEDs could be used and need not all have the same duty cycle relative to the measurement interval. Regulating the relative duty cycle of an LED to achieve a desired average spectral power distribution during a measurement interval can be used additionally or alternatively to regulating the LED's voltage and/or current or otherwise controlling its light intensity.

Although FIG. 8 illustrates yet another example of a method for measuring color, various changes may be made to FIG. 8. For example, while shown as a series of steps, various steps in FIG. 8 could overlap or occur in parallel. As a particular example, step 802 could occur in parallel with steps 804-806. Also, the method 800 could involve the use of one or multiple illuminating devices or measurement detectors.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory.

It may be advantageous to set forth definitions of certain words and phrases used throughout this patent document. The term "program" refers to one or more computer programs, software components, sets of instructions, procedures, functions, objects, classes, instances, related data, or a portion thereof adapted for implementation in a suitable computer code (including source code, object code, or executable code). The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A system, comprising:
    an illuminating device operable to generate light for illuminating a sample of material during a plurality of first illumination states, wherein the sample is illuminated differently during different ones of the first illumination states;
    a detector operable to detect light that has interacted with the sample during the first illumination states and to provide measurements of the light that has interacted with the sample during the first illumination states;
    a controller operable to adjust a duty cycle of the illuminating device to control the illumination of the sample during the first illumination states; and
    an analyzer operable to determine a spectral characteristic of the sample based on the measurements, wherein the determined spectral characteristic is associated with a second illumination state that is different than the first illumination states.

2. The system of claim 1, wherein the illuminating device includes at least one light emitting diode (LED).

3. The system of claim 2, wherein the illuminating device includes multiple LEDs, the controller operable to adjust the duty cycle of individual LEDs or groups of LEDs.

4. The system of claim 1, wherein:
    the illuminating device includes multiple illuminating devices; and
    the detector includes multiple detectors.

5. The system of claim 1, further comprising at least one backing positioned on an opposing side of the sample as the illuminating device.

6. The system of claim 1, wherein the second illumination state is not a linear combination of two or more of the first illumination states.

7. The system of claim 1, wherein the analyzer does not use, when determining the spectral characteristic of the sample, any measurement of light that has not interacted with the sample.

8. The system of claim 1, wherein the analyzer is further operable to control operation of the controller, thereby controlling the illumination of the sample.

9. The system of claim 1, wherein the analyzer is operable to determine the spectral characteristic of the sample by:
   determining an illuminator-independent radiance transfer factor of the sample; and
   determining a fluorescent emission spectrum of the sample using the radiance transfer factor.

10. The system of claim 1, wherein the spectral characteristic includes a color of the sample.

11. The system of claim 1, wherein the controller is further operable to adjust at least one of a voltage and a current for driving the illuminating device to control the illumination of the sample.

12. The system of claim 11, further comprising a reference detector operable to measure a spectral power distribution of the light generated by the illuminating device;
   wherein the analyzer is further operable to cause the controller to adjust at least one of the duty cycle, the voltage, and the current until the measured spectral power distribution is within a specified threshold of a desired spectral power distribution.

13. The system of claim 1, wherein:
   the measurement of the light that has interacted with the sample includes a spectral power distribution of the light that has interacted with the sample; and
   the duty cycle of the illuminating device represents a percentage of time that the illuminating device is generating light during a measurement interval.

14. A method, comprising:
   illuminating a sample of material using at least one light emitting diode (LED) during a plurality of first illumination states, wherein the sample is illuminated differently during different ones of the first illumination states;
   detecting light that has interacted with the sample during the first illumination states;
   providing measurements of the light that has interacted with the sample during the first illumination states;
   determining a spectral characteristic of the sample based on the measurements, wherein the determined spectral characteristic is associated with a second illumination state that is different than the first illumination states; and
   adjusting a duty cycle of the at least one LED to control the illumination of the sample.

15. The method of claim 14, wherein:
   illuminating the sample includes using multiple LEDs to illuminate the sample; and
   adjusting the duty cycle includes adjusting the duty cycle of individual LEDs or groups of LEDs.

16. The method of claim 14, wherein the second illumination state is not a linear combination of two or more of the first illumination states.

17. The method of claim 14, wherein determining the spectral characteristic of the sample includes determining the spectral characteristic of the sample without using any measurement of light that has not interacted with the sample.

18. The method of claim 14, further comprising adjusting at least one of a voltage and a current for driving the at least one LED to control the illumination of the sample.

19. The method of claim 18, further comprising:
   measuring a spectral power distribution of light generated by the at least one LED; and
   adjusting at least one of the duty cycle, the voltage, and the current until the measured spectral power distribution is within a specified threshold of a desired spectral power distribution.

20. A system, comprising:
   at least one light emitting diode (LED) operable to generate light for illuminating a sample of material during a plurality of first illumination states, wherein the sample is illuminated differently during different ones of the first illumination states;
   a detector operable to detect light that has interacted with the sample during the first illumination states and to provide measurements of the light that has interacted with the sample during the first illumination states;
   an analyzer operable to determine a spectral characteristic of the sample using the measurements, wherein the determined spectral characteristic is associated with a second illumination state that is different than the first illumination states; and
   a controller operable to adjust the at least one LED to control the illumination of the sample;
   wherein the analyzer, to determine the spectral characteristic of the sample, does not use any measurement of light that has not interacted with the sample.

21. The system of claim 20, wherein the controller is operable to adjust a duty cycle of the at least one LED.

* * * * *